United States Patent [19]
Salatka et al.

[11] Patent Number: 5,297,298
[45] Date of Patent: Mar. 29, 1994

[54] EYE SHIELD

[76] Inventors: Robert G. Salatka, 5461 Los Robles, Carlsbad, Calif. 92008; James H. Mitchell, 11025 Autillo Way, San Diego, Calif. 92127

[21] Appl. No.: 997,854

[22] Filed: Dec. 29, 1992

[51] Int. Cl.⁵ ............................................. A61F 9/02
[52] U.S. Cl. ................................................ 2/447; 2/9; 2/452
[58] Field of Search ............... 2/431, 439, 426, 427, 2/432, 446, 447, 448, 450, 9, 10, 12, 8, 13; 351/41, 44, 123, 110, 113; 128/857, 863

[56] References Cited

U.S. PATENT DOCUMENTS

| D. 170,033 | 7/1953 | Spencer . |
| 1,631,210 | 6/1927 | Johnson ................................ 2/12 |
| 1,706,667 | 3/1929 | Haustein ............................ 2/431 X |
| 1,884,047 | 10/1932 | McClellan . |
| 2,342,982 | 2/1944 | Stern et al. ............................ 2/9 |
| 2,527,027 | 10/1950 | Mull . |
| 2,614,255 | 10/1952 | Ellis . |
| 2,774,970 | 12/1956 | Du Bois ................................ 2/9 |
| 2,866,202 | 12/1958 | Landis . |
| 3,233,249 | 2/1966 | Baratelli et al. ................. 351/44 X |
| 4,670,915 | 6/1987 | Evans . |
| 4,815,838 | 3/1989 | Liautaud . |
| 4,843,655 | 7/1989 | Hegendorfer ..................... 2/439 X |
| 4,852,189 | 8/1989 | Duggan . |
| 4,884,296 | 12/1989 | Nix, Jr. . |
| 4,898,460 | 2/1990 | Magninat et al. . |
| 4,917,479 | 4/1990 | Bidgood ............................. 351/123 |
| 4,945,573 | 8/1990 | Landis ................................... 2/9 |
| 5,012,527 | 5/1991 | Michel ............................... 2/431 X |
| 5,113,529 | 5/1992 | Carr . |

FOREIGN PATENT DOCUMENTS

| 148616 | 2/1924 | France . |
| 1005015 | 12/1951 | France ................................. 2/12 |
| 0329470 | 5/1930 | United Kingdom .................. 2/12 |
| 432254 | 7/1935 | United Kingdom . |
| 435105 | 9/1935 | United Kingdom . |

Primary Examiner—Peter N. Nerbun
Attorney, Agent, or Firm—Jerry R. Seiler

[57] ABSTRACT

An eye shield comprises an elongated, flexible, spring-like frame member generally bowed along its length and biased toward an unsprung condition in which the ends are spaced apart a distance less than the width of a user's head, and a transparent, flexible eye covering member having a pair of first and second orifices for being removably secured on the frame member.

23 Claims, 2 Drawing Sheets

EYE SHIELD

BACKGROUND OF THE INVENTION

Transparent eye shields are especially useful in medical or dental surgical operations where the user's eyes may be exposed to blood-born pathogens such as Hepatitis, Staphylococcus and HIV viruses. Although such devices are available, they are constructed with the frame substantially permanently attached to or otherwise integral with the eye covering portion, which is typically of industrial grade plastic, suitable for protecting the eyes from flying debris, but unnecessarily thick and heavy for use in a medical or dental setting. Moreover, a lightweight sporting eye shield which can be easily assembled and disassembled for interchanging different lens is needed.

SUMMARY OF THE INVENTION

The present invention is directed to a relatively inexpensive, lightweight eye shield device for being worn on the face of the user composed of a substantially flexible and transparent eye covering member and a separate frame member on which the eye covering member is removably secured. The frame and lens components have features which provide for easily interchanging the lenses. The device of the invention may be made of relatively inexpensive materials, including flat transparent plastic sheet stock from which the eye covering member, which is bendable or formable for being secured on the frame member, is cut or stamped.

DETAILED DESCRIPTION

Figure 1:
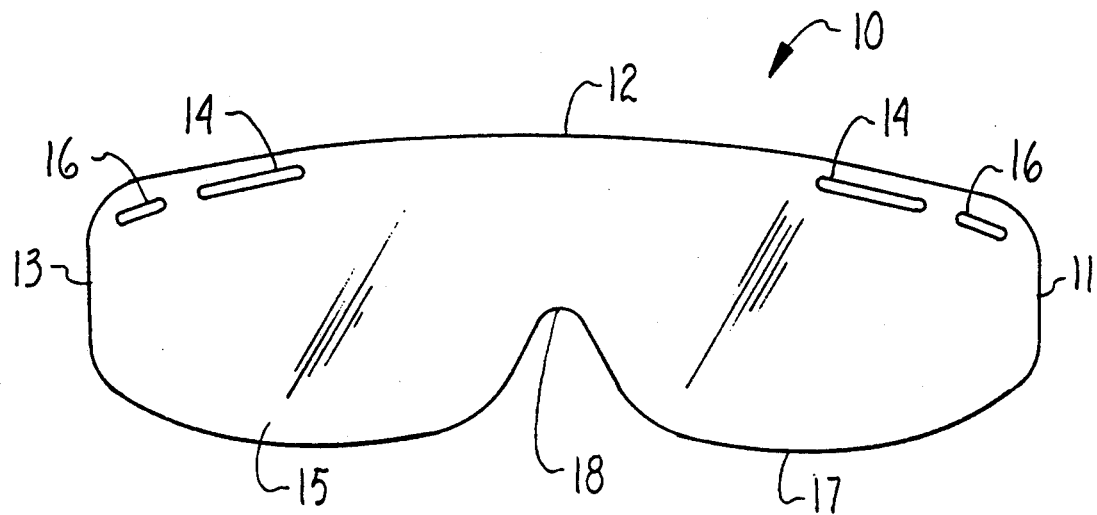
FIG. 1 is a plan view of the flat eye covering lens member.
Figure 2:
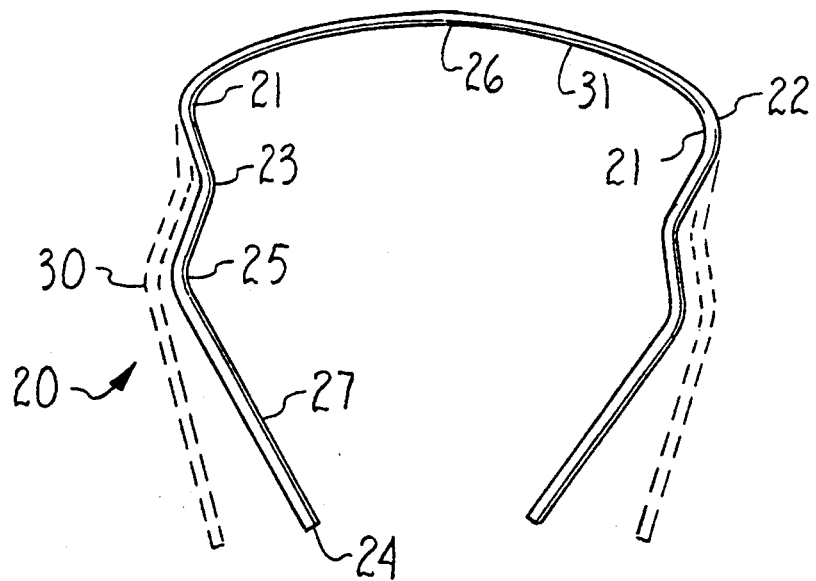
FIG. 2 is a top view of preferred embodiment of the frame member.

In FIGS. 1 and 2, there are shown the two components of the eye shield of the invention. In FIG. 1, the lens 10 comprises the eye covering member 15 which is transparent and flexible, and preferably made of a thin gauge material which is substantially transparent. Suitable materials include polyvinyl chloride, polyethylene, polypropylene, polystyrene, polycarbonate, acetate, cellulosic or acrylic plastic. The specific material used is not so critical although a material which does not fog, and is not easily scratched and/or finger printed is preferred. For example, polyester resin, although transparent, flexible and readily available and relatively inexpensive, scratches and finger prints rather easily. A preferred material comprises a polycarbonate resin, commercially available as Lexan ®, a thermoplastic carbonate-linked polymer produced by reacting bisphenol A and phosgene. However, other plastics, as described above, may also be used and where single use, disposable lens are intended, the less expensive plastics may be quite suitable. A preferred plastic is also relatively thin and commonly available in flexible sheets from which the eye covering member can be readily stamped or cut, without shattering, cracking, etc. The eye covering material s also preferably flexible so that it can be bowed to form to the users face with insignificant visual distortion. However, the use of a preformed, bowed eye covering member is not precluded, so long as it can be removably secured on the frame member for lens interchangeability. The eye covering member must also be of the length so that when secured in the frame member, it extends over the eyes to the user's temples, thereby offering significant protection at the side of the eyes with insignificant or virtually no visual distortion in the area of the bend or bow. Preferably, the thickness of the film for the eye covering member is less than about 40 mil, and preferably between about 7 and about 30 mil. The eye covering member may be clear, or polarized, or it may be treated for UV protection, tinted, smoked, mirrored, or coated for hardness, non-reflective, anti-fog, and the like.

As illustrated in FIG. 1, the eye covering member or lens 15 extends between a pair of opposite side edges 11 and 13, which are separated at a distance suitable so that the lens or eye covering extends to the users temples when the device is worn. The upper edge 12 extends along the user's forehead, usually at or above the eyebrows, with the lower edge 17 extending down to the user's cheeks, with notch 18 resting on or extending above the user's nose bridge.

An important feature of the eye covering lens member 15 is a pair of first and second openings, holes, or orifices 14 and 16, respectively, spaced downwardly from the upper edge 12, and preferably along or parallel therewith and aligned to each other. A first orifice 16 is preferably located adjacent or near each side edge, 11 and 13, with a second orifice 14 spaced between a first orifice 16 and the center of the eye covering member. The second orifices may be relatively close to the first orifices, in the embodiment shown in FIG. 2, or they may be spaced closer to the center of the eye covering member. The spacing and location of second orifices 14 will depend on the shape and cross-sectional dimensions of the frame member and its desired fit with the eye covering member. The shape of the orifices will also depend somewhat on the shape of the frame member, as will be explained more fully hereinafter. Using the preferred frame member shown in FIG. 2, the orifices are somewhat elongated to accommodate the bends in the frame member, as well as to provide ease for inserting the frame member through the orifices, and removable therefrom. The specific shape and dimensions of the first and second orifices are only important in that they should allow for easy insertion and removal of the frame member, and shapes other than those shown may be used.

FIG. 2 illustrates the frame member to which the eye covering member of FIG. 1 is secured. The frame member illustrated is the preferred embodiment, comprising a plastic, composite, or metal rod or tube made from a spring-like memory retaining material bowed along its length to form a U-shaped member extending from approximately the user's ears and along the forehead. Thus, the frame member 20 is preferably of a length sufficient so that it's two opposite ends 24 extend at least slightly beyond the user's ears and rest in the ear saddle when the device is placed on the user's head, and extends along the temples and across the user's forehead. Where an overall bowed or U-shaped frame is used, the location of the second orifices 14 relative to the side and center of the eye covering member may be selected to give a preferred or desired fit between the frame and eye covering members. Although the frame member may be U-shaped or simply continually bowed along its length, a disadvantage of such shapes is that the eye covering portion is hingedly movable on the frame when assembled, creating structural instability, whereby the lens could inadvertently slide upon, rotate or flip-up on the frame.

In a preferred embodiment, there is at least one pair of opposite bends 21 on opposite sides of a forehead portion 31. Moreover, the forehead covering portion 31 is also preferably bowed, at least slightly, so that it will conform generally to the shape of the user's forehead. Such a bowed condition may be a single general bow along the length of the forehead covering portion 31 between the two opposite bends 21, or may comprise a center bend 26 or a plurality of bends, or combination of a general bow and one or more bends. The side extensions or temple portions 27 of the frame member extending from each bend 21 and to an end 24 may be relatively straight or somewhat bowed, or may comprise a series of bends as illustrated in FIG. 2. In the preferred embodiment shown, a second bend 23 and third bend 25 are used, both second and third bends being preferably of an obtuse angle, with the smaller angle of second bend 23 facing opposite the bend 21, and the small angle of third bend 25 facing the same direction as first bend 21. The purpose of the additional bends 23 and 25 is to assist in better securing the eye covering member 10 on the frame 20. Thus, middle or second bend 23, which extends along the inside of the bow of the eye covering member when assembled, creates a "lock" preventing the lens from pivoting or otherwise being hingedly moved relative to the frame member. Yet, these bends do not interfere with the ease of assembly and lens interchangeability.

Although a rigid frame member could be used, the frame member is preferably formed of a light-weight spring-like plastic material such as polyethylene, polypropylene or PVC, which retains its memory to a first unsprung condition shown in FIG. 2 and which can be sprung to a second position or condition 30 shown in dashed lines, when the frame is placed on the user's head, and in which sprung condition, the opposite ends are urged or biased toward the original unsprung condition. Such a feature assists in securing the frame member and entire eye shield on the user's head as the bowed frame member is biased toward the direction of the unsprung condition whereby ends 24 are forced or urged against the user's head. Alternatively, the frame member may be made of similar spring-like materials such as metal, or of other suitable plastics, having such a feature. The disadvantage of using a rigid, non-spring frame member is that ear pieces or a tether or similar means must be used to prevent the frame from slipping or falling from the user's head, when the user leans down, or moves, as in a sports activity. Thus, such a rigid, non-spring frame member is not usually practical for general use, without such additional components for securing the frame on the user's head. The cross-sectional shape of the frame member may be varied, such as tubular, solid, flat, oval, rectangular, so long as the aforesaid characteristics and features are present. The second position 30 shown in FIG. 2 will vary in size and shape, depending on the head size of the user. Where the frame member is made from a spring-like plastic, a "living" hinge may be incorporated. Such a hinge is integrally formed on the plastic itself so that the hinge is a thin, flexible skin-like film portion of the plastic which may be repeatedly folded. This type of hinge may be formed along each of the temple portions 27 of the frame member, anywhere between first bend 21 and end 24. Such integrally formed plastic hinges may also be formed on the inside bow of the frame member so that they do not interfere with or defeat the biased function of the frame member as shown in FIG. 2. Such hinges, well known in the art, offer the advantage of being able to fold the side extensions inwardly toward the inside of the bow and in the plane of the frame member.

Figure 3:
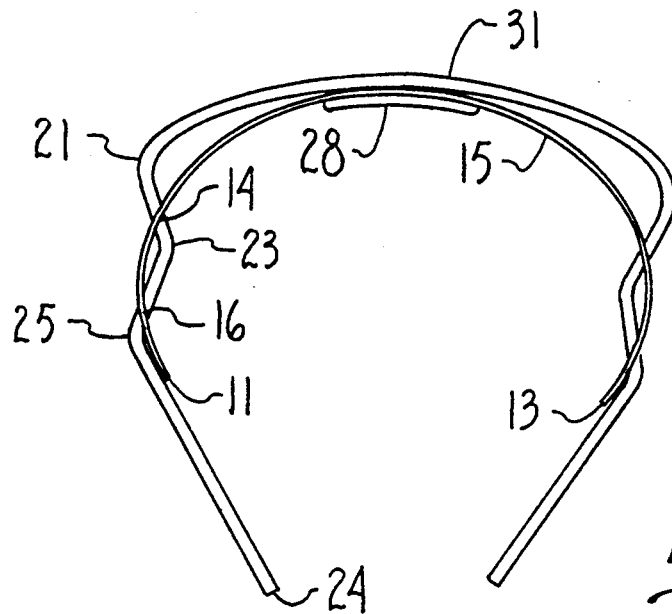
FIG. 3 is a top view showing the eye covering member of FIG. 1 secured to the frame member of FIG. 2.
Figure 4:
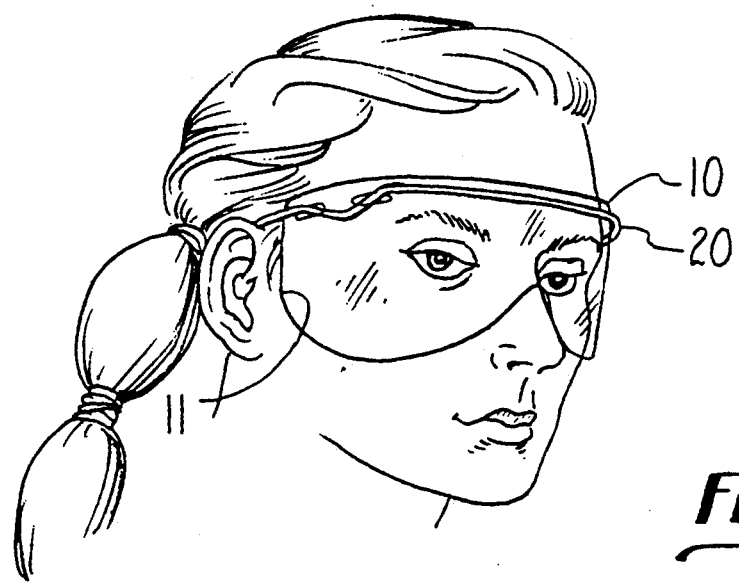
FIG. 4 illustrates the eye shield of the invention in position as worn by the user.

In FIG. 3, the assembled eye shield is shown, with the location of the first and second opposite orifices 16 and 14, respectively, shown relative to the first, second and third bends 21, 23 and 25, respectively, of the preferred frame member embodiment. In FIG. 4, the position of the device when worn by the user is also shown. It will be noted that the eye covering member extends beyond the user's eyes to the temple area whereby the sides of the user's eyes to the substantially protected from exposure to fluids, wind, dust, etc.

The device of the invention offers advantages and a variety of uses over previous eye covering devices. Because the device is so light-weight it is not as easily displaced or dislodged from the user's head even during exercise or similar activity. Moreover, by incorporating a single unitary frame member, there are no mechanical hinges to be maintained or repaired. The device also provides easy packaging and storage because of the substantially flat eye covering member, and yet it can be easily and readily assembled and disassembled. Thus, the user may wish to carry or utilize a variety of different interchangeable eye covering members, such as clear, tinted, UV protected, polarized, etc., each of which may be selected and easily secured on and removed from the frame member, as desired. Such lens interchangeability is of significant advantage for sports and recreational use, where light and/or weather conditions change during the day dictating the use of different lens to satisfy the user's requirements. The device is also easily fitted on the user's head without the use of a fastener and provides a wrap-around, light-weight, distortion free viewing lens which extends substantially to the side of the user's eyes thereby offering additional protection from fluids, dust, or the like contacting or impinging on the eyes from the side. Such a feature is not only important in medical or dental operating room environments for protecting contact between the surgical staff and patient to reduce risk of transferring fluidborn pathogens, but offers protection during recreational use, such as bike riding, running, jogging, or in more casual recreational use where sand or dust may be blowing, regardless of the activity of the user.

Figure 5:
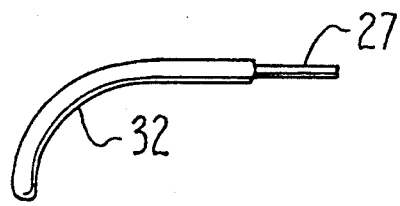
FIG. 5 shows a portion of the frame member with an ear piece removably secured on an end thereof.

In addition to the two necessary components of the device illustrated in FIGS. 1 and 2, additional or optional features or components may be used and attached to the device. For example, in FIG. 3, a cushion 28, in the form of one or more elongated pieces or strips 28, comprising foam plastic or rubber, preferably lightweight sponge material having an adhesive along one surface, may be placed along the upper edge 12 of the eye covering member 10, thereby offering a cushion between the eye covering member and the user's forehead. Such material is inexpensive and is readily available in rolls and may be easily cut to the desired length. Removable ear pieces 32 may also be used for being secured at the ends of the frame member, a portion of the ear piece length 27 as illustrated in FIG. 5. Such ear pieces are especially useful on a rigid frame member as previously described and where there is a special need for the eye shield being maintained on the user's face without the danger of slipping off during a surgical procedure, or in a recreational activity where security of the device on the user's head is of significant importance. These as well as other features of the device within the purview of the invention will be evident to those skilled in the art.

We claim:

1. An eye shield comprising:
   an eye covering member comprising a substantially transparent, flexible member having an upper edge for extending along a user's forehead from opposite first and second side edges between the user's temples and a lower edge for extending across a user's face and forming an eye shielding lens between said upper and lower edges, and a pair of first and second orifices located adjacent to said upper edge, each of said first orifices located adjacent to said first and second side edges, respectively, and each of second orifices spaced from said first orifices toward the center of said eye covering member, and
   a frame member for securing said eye covering member on the face of a user, comprising an elongated flexible, spring-like shaft generally bowed along its length between opposite frame member ends thereof and biased toward a first unsprung condition having said opposite frame member ends spaced apart a distance less than the width of the user's head between the ears, wherein said frame member is formed along its length with a pair of opposite first bends and a forehead portion extending therebetween, a pair of opposite second bends each located between a different one of said first bends and a different one of said opposite frame member ends, and a pair of opposite third bends each located between a different one of said second bends and a different one of said opposite frame member ends.
   said flexible eye covering member being removably secured on said frame member, said shaft extending through each of said first and second orifices, wherein said secured eye covering member is generally bowed for following a generally bowed contour of a user's face and forehead, wherein said forehead portion, said first bends and said third bends of said frame member are positioned on the outside of the bow of said eye covering member, and wherein said second bends of said frame member are positioned on the inside of the bow of said eye covering member, said eye covering member being capable of being secured on a user's face with said frame member extending along a user's forehead with said opposite ends urged apart from said first condition to a second condition against opposite sides of the user's head, and wherein said eye covering portion extends downwardly from said upper edge over the user's eyes.

2. The eye shield of claim 1 wherein said forehead portion of said frame member has a middle bend therealong between said first bends.

3. The eye shield of claim 1 wherein said frame member comprises a single length of plastic and wherein each of said temple portions include an integral plastic film hinge located on the inside of the bow of the frame member.

4. An eye shield comprising:
   an eye covering member comprising a substantially transparent, flexible member having an upper edge for extending along a user3 s forehead from opposite first and second side edges between the user's temples, and a pair of first and second orifices located adjacent to said upper edge, said first and second orifices being elongated in a direction generally parallel with said upper edge, each of said first orifices located adjacent to said first and second side edges, respectively, and each of second orifices spaced from said first orifices toward the center of said eye covering member, and
   a frame member for securing said eye covering member on the face of a user, comprising an elongated flexible, spring-like shaft generally bowed along its length between opposite frame member ends thereof and biased toward a first unsprung condition having said opposite frame member ends spaced apart a distance less than the width of the user's head between the ears,
   said flexible eye covering member being removed secured on said frame member, said shaft extending through each of said first and second orifices, said eye covering member being capable of being secured on a user's face with said frame member extending along a user's forehead with said opposite ends urged apart from said first condition to a second condition against opposite sides of the user's head, and wherein said eye covering portion extends downwardly from said upper edge over the user's eyes.

5. The eye shield of claim 4 wherein said frame member is formed along its length with a pair of opposite first bends having a forehead portion extending therebetween and opposite temple portions extending from each first bend to one of said frame member ends.

6. The eye shield of claim 5 wherein said forehead portion is bowed between said first bends.

7. The eye shield of claim 5 wherein said forehead portion has a middle bend therealong between said first bends.

8. The eye shield of claim 5 wherein said eye covering member is secured on said frame member with said eye covering member generally bowed between said opposite side edges with the inside of the bow for extending around a portion of the user's head, and wherein the forehead portion of said frame member extends along the opposite side of said eye covering member from the inside of said bow of said eye covering member.

9. The eye shield of claim 1 wherein said first and second orifices are elongated in a direction generally parallel with said upper edge.

10. The eye shield of claim 5 wherein said first bends are located on the outside of said bow of said eye covering member.

11. The eye shield of claim 5 wherein said frame member includes a pair of opposite second bends, each located between one of said first bends and one of said opposite ends, and a pair of opposite third bends, each located between one of said second bends and one of said opposite ends, said second bends each forming a substantially similar angle and located on the inside of said bow of said eye covering member, and said third bends each forming a substantially similar angle on the outside of said bow of said eye covering member.

12. The eye shield of claim 8 wherein said first bends each form a substantially similar angle and located on the outside of said bow of said eye covering member.

13. The eye shield of claim 12 wherein said frame member includes a pair of opposite second bends, each located between one of said first bends and one of said opposite frame member ends, and a pair of opposite third bends, each located between one of said second bends and one of said frame member opposite ends, said second bends each forming a substantially similar angle and located on the inside of said bow of said eye covering member, and said third bends each forming a substantially similar angle and located on the outside of said bow of said eye covering member.

14. The eye shield of claim 5 including an ear piece member removably secured to each of said frame member ends.

15. The eye shield of claim 5 wherein said eye covering member comprises a sheet of plastic material having a lower edge having a notch formed therealong for overlying the bridge of a user's nose.

16. The eye shield of claim 15 wherein said eye covering member comprises opposite eye covering sections extending between said notch and said side edges for substantially overlying a user's facial cheeks and temples.

17. The eye shield of claim 5 wherein said frame member comprises a single length of plastic and wherein each of said temple portions include an integral plastic film hinge located on the inside of the bow of the frame member.

18. An eye shield comprising:
an eye covering member comprising a substantially transparent member having an upper edge for extending along a user's forehead from opposite first and second side edges between the user's temples, and a pair of first and second orifices located adjacent to said upper edge, each of said first orifices located adjacent to said first and second side edges, respectively, and each of second orifices spaced from said first orifices toward the center of said eye covering portion, and
a frame member for securing said eye covering portion on the face of a user, comprising an elongated shaft generally bowed along its length between opposite frame member ends thereof and having a pair of first opposite bends and a forehead portion extending therebetween, a pair of opposite second bends, each located between one of said first bends and one of said opposite frame member ends, and a pair of opposite third bends, each located between one of said second bends each forming a substantially similar angle and located on the inside of said bow of said eye covering member, and said third bends each forming a substantially similar angle and located on the outside of said bow of said eye covering member,
said eye covering portion being removably secured on said frame member, said shaft extending through each of said first and second orifices, said eye covering member being capable of being secured on a user's face with said frame member extending along a user's forehead with said opposite ends located on opposite sides of the user's head, and wherein said eye covering portion extends downwardly from said upper edge over the user's eyes.

19. The eye shield of claim 1 wherein said forehead portion of said frame member is bowed between said first bends.

20. The eye shield of claim 1 wherein said forehead portion has a middle bend therealong between said first bends.

21. The eye shield of claim 5 including an ear piece secured to each of said frame member ends.

22. The eye shield of claim 18 including an ear piece secured on each of said opposite frame member ends.

23. The eye shield of claim 18 including tether member secured to each of said opposite frame member ends.

* * * * *

UNITED STATES PATENT AND TRADEMARK OFFICE
CERTIFICATE OF CORRECTION

PATENT NO.    : 5,297,298
DATED         : March 29, 1994
INVENTOR(S)   : Robert G. Salatka and James H. Mitchell It is certified that error appears in the above-identified patent and that said Letters Patent is hereby corrected as shown below:

Column 2,
Line 1, "s" should be -- is --; and

Column 4,
Line 20, "To" should be -- are --

Column 6,
Line 4, "user3s" should be -- user's --; and

Column 8,
Line 12, after "bends" and before "each" should be inserted -- and one of said frame member opposite ends, said second bends --

Signed and Sealed this

First Day of April, 2003

JAMES E. ROGAN
*Director of the United States Patent and Trademark Office*